(12) United States Patent
Kotlarchik

(10) Patent No.: US 8,944,813 B2
(45) Date of Patent: Feb. 3, 2015

(54) SYSTEM FOR DETECTION, TREATMENT AND COVERAGE FEEDBACK OF ORAL HEALTH CONDITIONS

(75) Inventor: Garrett Kotlarchik, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 184 days.

(21) Appl. No.: 13/060,291

(22) PCT Filed: Aug. 12, 2009

(86) PCT No.: PCT/IB2009/053569
§ 371 (c)(1),
(2), (4) Date: Feb. 23, 2011

(87) PCT Pub. No.: WO2010/023582
PCT Pub. Date: Mar. 4, 2010

(65) Prior Publication Data
US 2011/0159453 A1   Jun. 30, 2011

Related U.S. Application Data

(60) Provisional application No. 61/091,447, filed on Aug. 25, 2008.

(51) Int. Cl.
*A61C 1/00* (2006.01)
*A61C 17/22* (2006.01)
*A61B 5/00* (2006.01)
*A61B 1/24* (2006.01)

(52) U.S. Cl.
CPC .............. *A61C 17/22* (2013.01); *A61B 5/0088* (2013.01); *A61B 1/24* (2013.01)

USPC ................................................ 433/27; 433/29

(58) Field of Classification Search
USPC ................... 433/29–31, 80–81, 88–89, 215; 15/22.1, 22.2; 606/88, 89
See application file for complete search history.

(56) References Cited

U.S. PATENT DOCUMENTS 5,378,153 A   1/1995   Giuliani et al.
5,742,700 A * 4/1998   Yoon et al. ................... 382/132

(Continued)

FOREIGN PATENT DOCUMENTS

EP   1101436 A2   5/2001
EP   1693021 A1   8/2006

(Continued)

*Primary Examiner* — Yogesh Patel

(57) ABSTRACT

The oral health appliance (10) includes a source of light (16) having a wavelength which is suitable for determination of oral health conditions, as well as treatment thereof. An assembly (16) in the appliance directs the light to selected dental regions of the mouth. A light receiver and sensor (16) receives reflected light from the dental regions, produces signal information therefrom and delivers the signal information to a processor (20), which determines the presence of oral health conditions, as well as determining the overall coverage of the mouth during a use of the appliance. The information from the processor is then sent to a display (24), identifying the presence of any oral health conditions and the location thereof, as well as information concerning those areas of the mouth which have been investigated during the use of the appliance and those which have not. The appliance includes a light system (34, 36, 38; 72, 74 76), a brushing system (64, 66, 68) and a fluid delivery system (94, 96, 98, 100) for treatment of any oral health condition identified.

13 Claims, 5 Drawing Sheets

(56) References Cited

U.S. PATENT DOCUMENTS

| | | | |
|---|---|---|---|
| 5,755,571 A * | 5/1998 | Companion | 433/72 |
| 6,102,704 A * | 8/2000 | Eibofner et al. | 433/215 |
| 6,276,934 B1 * | 8/2001 | Rakocz | 433/29 |
| 6,485,300 B1 * | 11/2002 | Muller et al. | 433/29 |
| 6,769,911 B2 | 8/2004 | Buchalla et al. | |
| 7,324,661 B2 | 1/2008 | Kemp et al. | |
| 2002/0064751 A1 * | 5/2002 | Lehmann | 433/26 |
| 2004/0236232 A1 | 11/2004 | Jonusauskas et al. | |
| 2005/0003323 A1 * | 1/2005 | Katsuda et al. | 433/29 |
| 2005/0287490 A1 * | 12/2005 | Stookey et al. | 433/29 |
| 2006/0240377 A1 | 10/2006 | De Josselin De Jong et al. | |
| 2007/0154863 A1 * | 7/2007 | Cai et al. | 433/89 |
| 2007/0259309 A1 * | 11/2007 | West et al. | 433/29 |

FOREIGN PATENT DOCUMENTS

| | | |
|---|---|---|
| WO | 2006125203 A2 | 11/2006 |
| WO | 2008018804 A1 | 2/2008 |

* cited by examiner

| Jaw | Teeth | Dimension | Mean (mm) | Std. Dev. (mm) | Range (mm) | Max (mm) | Min (mm) | n |
|---|---|---|---|---|---|---|---|---|
| Maxilla (upper jaw) | Central Incisors | Mesio-Distal Crown Diameter | 8.19 | 0.49 | 2.07 | 9.17 | 7.1 | 109 |
| | Central Incisors | Bucco-Lingual Crown Diameter | 6.62 | 0.58 | 1.33 | 8.03 | 6.7 | 133 |
| | Central Incisors | Crown Length | 10.57 | 0.88 | 3.7 | 12.47 | 8.77 | 32 |
| | Lateral Incisors | Mesio-Distal Crown Diameter | 6.52 | 0.53 | 2.66 | 7.51 | 4.86 | 108 |
| | Lateral Incisors | Bucco-Lingual Crown Diameter | 5.88 | 0.59 | 1.97 | 7.4 | 5.43 | 132 |
| | Lateral Incisors | Crown Length | 9.53 | 0.69 | 2.57 | 11 | 8.37 | 27 |
| | Cuspid | Mesio-Distal Crown Diameter | 7.55 | 0.39 | 1.9 | 8.34 | 6.5 | 105 |
| | Cuspid | Bucco-Lingual Crown Diameter | 7.31 | 0.63 | 2.27 | 9.2 | 7 | 125 |
| | Cuspid | Crown Length | 10.3 | 1.23 | 4.77 | 13.2 | 8.43 | 34 |
| | First Premolar | Mesio-Distal Crown Diameter | 7.18 | 0.39 | 1.5 | 7.88 | 6.38 | 93 |
| | First Premolar | Bucco-Lingual Crown Diameter | 9.25 | 0.52 | 1.73 | 10.03 | 8.3 | 80 |
| | First Premolar | Crown Length | 8.47 | 0.7 | 2.57 | 9.9 | 7.33 | 24 |
| | Second Premolar | Mesio-Distal Crown Diameter | 6.88 | 0.4 | 1.94 | 7.84 | 5.9 | 89 |
| | Second Premolar | Bucco-Lingual Crown Diameter | 9.15 | 0.57 | 2.23 | 10.23 | 8 | 74 |
| | Second Premolar | Crown Length | 7.93 | 0.8 | 2.67 | 9.33 | 6.67 | 33 |
| | First Molar | Mesio-Distal Crown Diameter | 9.65 | 0.51 | 2.31 | 10.86 | 8.54 | 112 |
| | First Molar | Bucco-Lingual Crown Diameter | 10.53 | 0.56 | 1.83 | 12.47 | 10.63 | 146 |
| | First Molar | Crown Length | 7.97 | 0.62 | 2.2 | 9.1 | 6.9 | 31 |
| | Second Molar | Mesio-Distal Crown Diameter | 9.61 | 0.58 | 2.79 | 10.89 | 8.1 | 91 |
| | Second Molar | Bucco-Lingual Crown Diameter | 10.43 | 0.76 | 2.4 | 12.8 | 10.4 | 114 |
| | Second Molar | Crown Length | 7.83 | 0.68 | 2.63 | 8.97 | 6.33 | 27 |
| | Third Molar | Mesio-Distal Crown Diameter | 8.8 | 0.67 | 3.3 | 10.65 | 7.35 | 30 |
| | Third Molar | Bucco-Lingual Crown Diameter | 10.7 | 0.87 | 5.15 | 13.5 | 8.35 | 30 |
| | Third Molar | Crown Length | 6.75 | 0.68 | 3 | 8.25 | 5.25 | 30 |

FIG. 4

| Jaw | Teeth | Dimension | Mean (mm) | Std. Dev. (mm) | Range (mm) | Max (mm) | Min (mm) | n |
|---|---|---|---|---|---|---|---|---|
| Mandible (lower jaw) | Central Incisors | Mesio-Distal Crown Diameter | 5.16 | 0.32 | 1.39 | 5.73 | 4.34 | 106 |
| | Central Incisors | Bucco-Lingual Crown Diameter | 5.31 | 0.39 | 1 | 6.57 | 5.57 | 121 |
| | Central Incisors | Crown Length | 9.17 | 1.04 | 3.93 | 11.23 | 7.3 | 18 |
| | Lateral Incisors | Mesio-Distal Crown Diameter | 5.7 | 0.37 | 1.66 | 6.49 | 4.83 | 109 |
| | Lateral Incisors | Bucco-Lingual Crown Diameter | 5.62 | 0.43 | 1.27 | 7.07 | 5.8 | 130 |
| | Lateral Incisors | Crown Length | 9.8 | 0.64 | 3.37 | 11.5 | 8.13 | 17 |
| | Cuspid | Mesio-Distal Crown Diameter | 6.63 | 0.4 | 1.96 | 7.56 | 5.6 | 107 |
| | Cuspid | Bucco-Lingual Crown Diameter | 6.8 | 0.65 | 2.93 | 9 | 6.07 | 125 |
| | Cuspid | Crown Length | 10.77 | 0.94 | 3.27 | 12 | 8.73 | 14 |
| | First Premolar | Mesio-Distal Crown Diameter | 7.14 | 0.43 | 1.6 | 7.9 | 6.3 | 95 |
| | First Premolar | Bucco-Lingual Crown Diameter | 7.76 | 0.46 | 1.43 | 8.33 | 7.03 | 80 |
| | First Premolar | Crown Length | 8.4 | 0.77 | 2.8 | 9.73 | 6.87 | 18 |
| | Second Premolar | Mesio-Distal Crown Diameter | 7.36 | 0.45 | 2.12 | 8.44 | 20.18 | 88 |
| | Second Premolar | Bucco-Lingual Crown Diameter | 8.32 | 0.5 | 1.9 | 9.2 | 7.3 | 66 |
| | Second Premolar | Crown Length | 8.37 | 0.62 | 4.2 | 9.93 | 7.07 | 17 |
| | First Molar | Mesio-Distal Crown Diameter | 10.39 | 0.51 | 2.03 | 11.41 | 9.39 | 110 |
| | First Molar | Bucco-Lingual Crown Diameter | 9.53 | 0.57 | 2.4 | 11.97 | 9.57 | 142 |
| | First Molar | Crown Length | 8.1 | 0.68 | 3.3 | 10.27 | 6.97 | 34 |
| | Second Molar | Mesio-Distal Crown Diameter | 10.41 | 0.6 | 2.5 | 11.93 | 9.43 | 89 |
| | Second Molar | Bucco-Lingual Crown Diameter | 9.66 | 0.55 | 1.83 | 11.17 | 9.33 | 116 |
| | Second Molar | Crown Length | 8.03 | 0.74 | 3.43 | 10.23 | 6.8 | 37 |
| | Third Molar | Mesio-Distal Crown Diameter | 11 | 0.6 | 3.15 | 12.4 | 9.25 | 29 |
| | Third Molar | Bucco-Lingual Crown Diameter | 10.05 | 0.51 | 1.6 | 10.65 | 9.05 | 29 |
| | Third Molar | Crown Length | 7.2 | 0.56 | 2.25 | 8.5 | 6.25 | 29 |

FIG. 5

SYSTEM FOR DETECTION, TREATMENT AND COVERAGE FEEDBACK OF ORAL HEALTH CONDITIONS

TECHNICAL FIELD

This invention relates generally to systems and methods which concern selected oral health conditions, such as plaque, caries, periodontitis and other conditions, and more specifically concerns a system and method using light which is capable of carrying out multiple functions relating to those oral health conditions.

BACKGROUND OF THE INVENTION

Detection and also treatment of various oral health conditions using light are generally known. Such systems, however, are typically found in a professional dental office. Such systems also often require two or more light sources. The systems are generally sophisticated, too expensive for home use, and usually require training for proper use. Further, such systems do not have the capability of determining which dental areas have actually been investigated for detection and/or actually treated and then to create a history of such activity. The dental professional using the equipment is highly trained and is able to easily visually determine what areas have been investigated for detection and/or treated. A home user would not be able to determine the extent of coverage with the conventional dental office equipment.

Reference sensors have been used in some cases to provide a determination of actual coverage for various oral treatment systems, but such systems are generally awkward and/or uncomfortable to use and expensive to implement. Further, such sensors have not been used in light-based detection/treatment systems.

Accordingly, there is a need for a relatively simple, straightforward appliance which can accomplish multiple oral care functions using light, including providing reliable feedback information to the user relative to thorough exploration/coverage of detection and treatment functions of the appliance. Such a system should be suitable for home use by a non-professional.

SUMMARY OF THE INVENTION

Accordingly, an oral care appliance for investigation of the mouth is disclosed, comprising: a source of light having a wavelength suitable for oral health condition diagnosis and/or treatment; an assembly for directing the light to the dental region of the mouth, covering one or more teeth; a light receiver or camera and sensor assembly for receiving light reflected from the teeth, the sensor providing output signal information corresponding to the reflected light; a processor for identifying the presence of an oral care condition from the output signal information and for using the output signal information to determine coverage of the dental region by the light; and a display for providing to the user information concerning any oral health conditions which have been identified by the microprocessor and information concerning coverage of the dental region.

Also disclosed is a method of oral care for the mouth with an appliance, comprising the steps of: generating light having a wavelength suitable for oral care condition diagnosis and transmitting said light to a selected oral dental surface; receiving reflected light from the oral dental surface; processing the reflected light to determine the presence of an oral health condition and to determine coverage of the oral dental surface of the mouth by the light as the user moves the appliance in the mouth; and displaying to the user information concerning the presence of oral health conditions which have been identified and the coverage of the oral dental surface achieved.

BRIEF DESCRIPTION OF THE DRAWINGS

FIGS. 4 and 5 are tables which show information concerning the size and location of the teeth in the upper and lower jaws, respectively.

BEST MODE FOR CARRYING OUT THE INVENTION

The system and method described herein involves the use of a single light source or possibly multiple light sources to investigate the dental areas of the mouth so as to detect various oral health conditions, treat those conditions and, further, provide information back to the user relative to the dental areas which were investigated and treated, if treatment was in fact carried out, during use of the appliance, and further indicate which dental areas, if any, were not covered.

Figure 1:
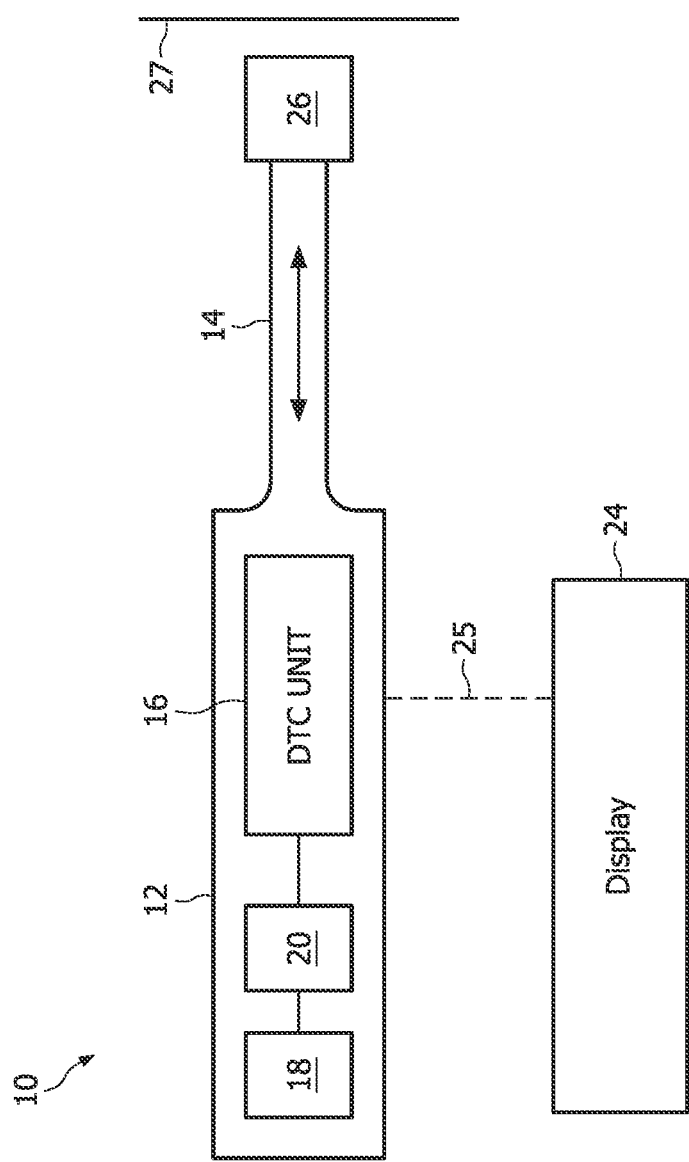
FIG. 1 is a simplified schematic drawing showing the overall concept of the present system.

FIG. 1 shows a simplified illustration of the system involving an appliance 10, which has a body portion 12 and an extended wand portion 14. Within body portion 12 is a detection-investigation/treatment/coverage (DTC) unit 16, a power source 18 for the appliance and a microprocessor control device 20. Information developed by the DTC unit 16 is provided to a display station 24, typically by wireless communication, indicated at 25. In basic operation, following investigation of a given dental region (usually one or two teeth) and processing of the resulting information, the user will be provided information on the type and location of any oral health condition in the dental region investigated which needs attention, as well as information on possible options provided by the appliance to treat the condition.

Further information is provided by the microprocessor 20 to the display station 24 as to which regions of the mouth have, and which regions have not, been investigated. This information allows the user to move the appliance to the appropriate dental region to be treated and to deliver a selected treatment. It also enables the user to go back to those regions which have not been previously investigated or were missed in an initial investigation.

Wand portion 14 of the appliance includes an applicator 26, shown in generalized form. The light from the DTC unit 16 is applied from the applicator 26 to the oral surface 27 being investigated. Reflected light is received back through the applicator 26, through the wand assembly to the DTC unit 16 to the microprocessor 20. The applicator could for example comprise a set of bristles for scrubbing the teeth as well as an outlet for fluid which can be used for treatment of selected dental conditions. All of the above is explained in more detail below.

Figure 2:
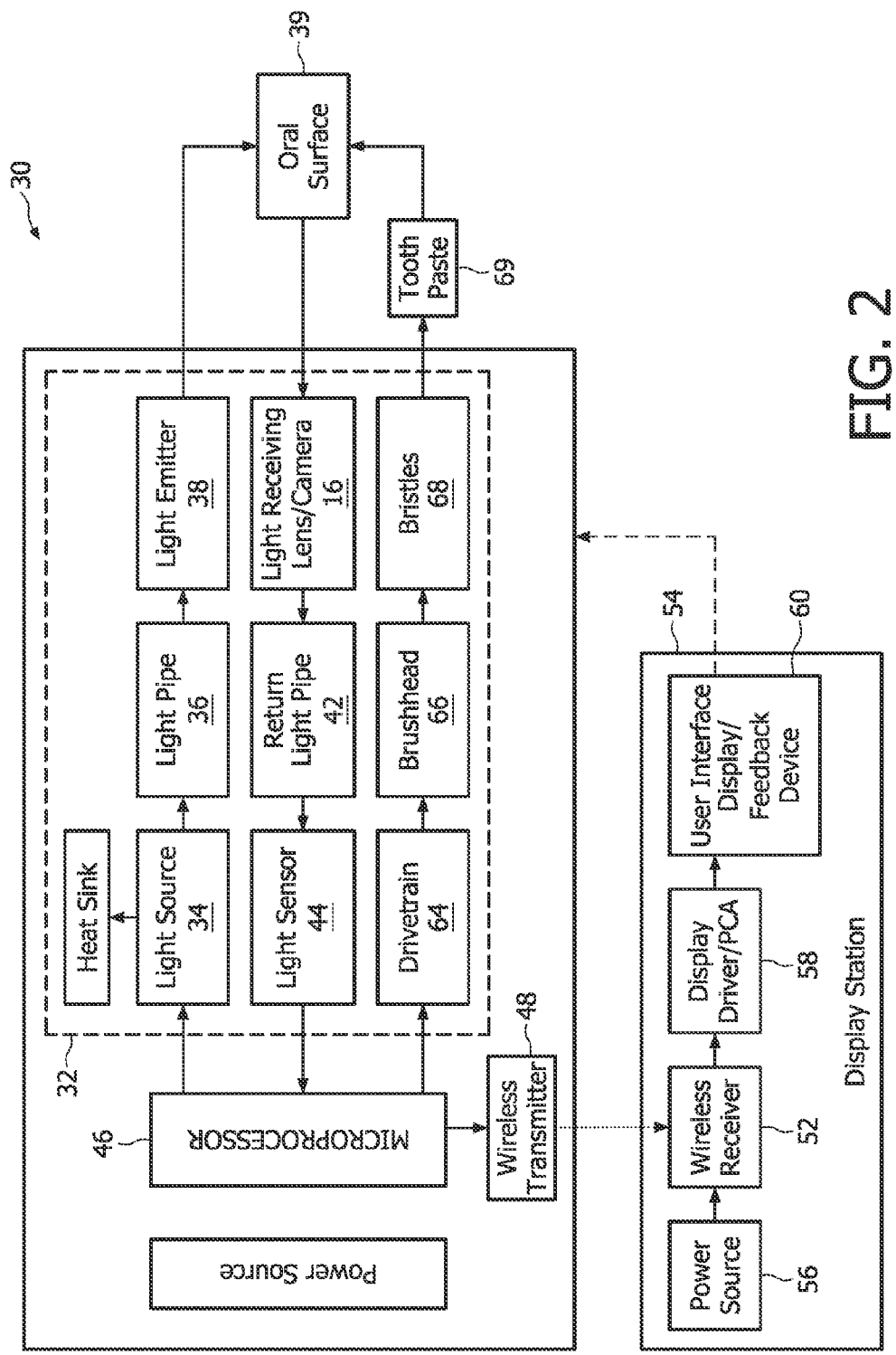
FIG. 2 is a block diagram showing the present system for the detection and treatment of plaque.

FIG. 2 is a block diagram of a hand held appliance 30 which is specifically adapted to sense and treat plaque. The appliance 30 includes a DTC unit 32 which includes a number of elements. A light source 34, which could be a laser or an LED, producing a light beam which has a wavelength which can be used to detect plaque. A blue light with a wavelength of 400-500 nm is one example, although other wavelengths can be used, including some in the red spectrum The light is applied to a transmit light pipe 36 in wand 14 and then to a light emitter 38, which is in the applicator. The light from the emitter 38 is directed to a specific dental/oral surface region 39. The region would typically be fairly small, for instance approximately 5 mm in diameter.

The light will fluoresce the plaque with some light being absorbed by the plaque and other light being reflected back to a light-receiving lens/camera in the applicator 16. This received light is directed to a return light pipe 42, then to a light sensor 44. The reflected light, in terms of wavelength or other characteristics such as energy level, can be associated with a particular oral condition, such as the presence or lack of plaque. The output of the light sensor is applied to microprocessor 46, which analyzes the light to determine the presence of plaque in the area covered by the transmitted light on the oral surface 39. The determination of the presence of plaque in the area covered is then applied to the wireless transmitter 48, which transmits the information to a wireless receiver 52 in a display station 54. The transmission of such information can be made on an area by area basis or can be delayed until the entire dental region has been investigated The display station will be typically located a short distance from the hand-held appliance itself, such as on a counter. The display station 54 also includes a power source 56 for the wireless receiver. The signal from the receiver 52 is then applied to a display driver 58 which interfaces with a display/feedback device 60. The display/feedback device 60 can take various forms, but will provide information which can be read, viewed or otherwise interpreted by the user concerning the presence of plaque in a specific dental area or areas.

The user then has the opportunity in one embodiment to provide instructions back to the hand-held appliance to deliver treatment to the dental area with the plaque. These instructions are applied to microprocessor 46, which electrically activates a drive train 64 in the appliance, which in turn moves a brushhead assembly 66 having bristles mounted 68 thereon. Toothpaste 69 or other dentifrice is typically added to the bristles, and the user then has the opportunity to brush the area having the detected plaque. A sensitizing solution may also be used which increases the effectiveness of the dentifrice. Various brushhead assembly arrangements can be utilized, including brushheads which operate in the sonic frequency range, i.e. 262±30 Hz. One example of such a drive train/brushhead assembly arrangement is shown in U.S. Pat. No. 5,378,153, which is owned by the assignee of the present invention, the contents of which are hereby incorporated by reference. Other drive train/brushhead arrangements can, of course, be used.

As briefly described above, the appliance also has the basic capability of using light to provide feedback to the user in terms of which areas of the dental region have been investigated or explored, i.e. which teeth the appliance has actually looked at and which areas still need to be explored/investigated. The microprocessor includes, in memory, information concerning typical teeth size and location in the mouth. This information is in the form of a look-up table. FIG. 4 shows in table form an example of known typical teeth size and location information for the upper jaw, while FIG. 5 shows a table with similar information for the lower jaw. This includes various dimensional information, including size ranges for each tooth, including, as shown in the tables, incisors, cuspids, pre-molars and first, second and third molars. The dimensional information includes the crown diameters and length of each portion of the tooth.

The microprocessor also includes an algorithm which processes the returning light information received by a camera 16, to identify pixel count and matches the pattern of intensity of the returning light relative to the stored tooth size information, to determine the particular tooth being illuminated and hence the location of the light beam in the mouth. The microprocessor can then determine which teeth have actually been investigated and which teeth have been missed. This information is then provided by the microprocessor to the wireless transmitter for communication to the display station. The user thus is provided feedback, not only on the location of any dental condition areas which need treatment, but also information on which areas of the mouth have been investigated, even if no conditions needing treatment were found. Accordingly, those areas which were deliberately not investigated or were overlooked are identified, so that the user can go to those specific areas if desired.

Hence, with FIG. 2, using a single light source, with a drive train/brushhead bristle assembly incorporated in the appliance, plaque conditions can be accurately located and treated, as well as coverage information obtained. The appliance 10 can be used to determine the presence of plaque, or lack thereof, throughout the mouth, with the coverage capability of the appliance, also referred to as mapping, providing assurance that the entire dental region has been investigated. Those areas which need treatment for plaque are identified and displayed to the user. The user will then locate the problem areas and provide treatment for those areas with the appliance in the treatment mode, which for plaque will typically be brushing with toothpaste or other dentifrice, although other treatment possibilities, including light treatment, can be used. Use of light for treatment as well as in detection is discussed in more detail below in connection with other oral conditions.

Figure 3:
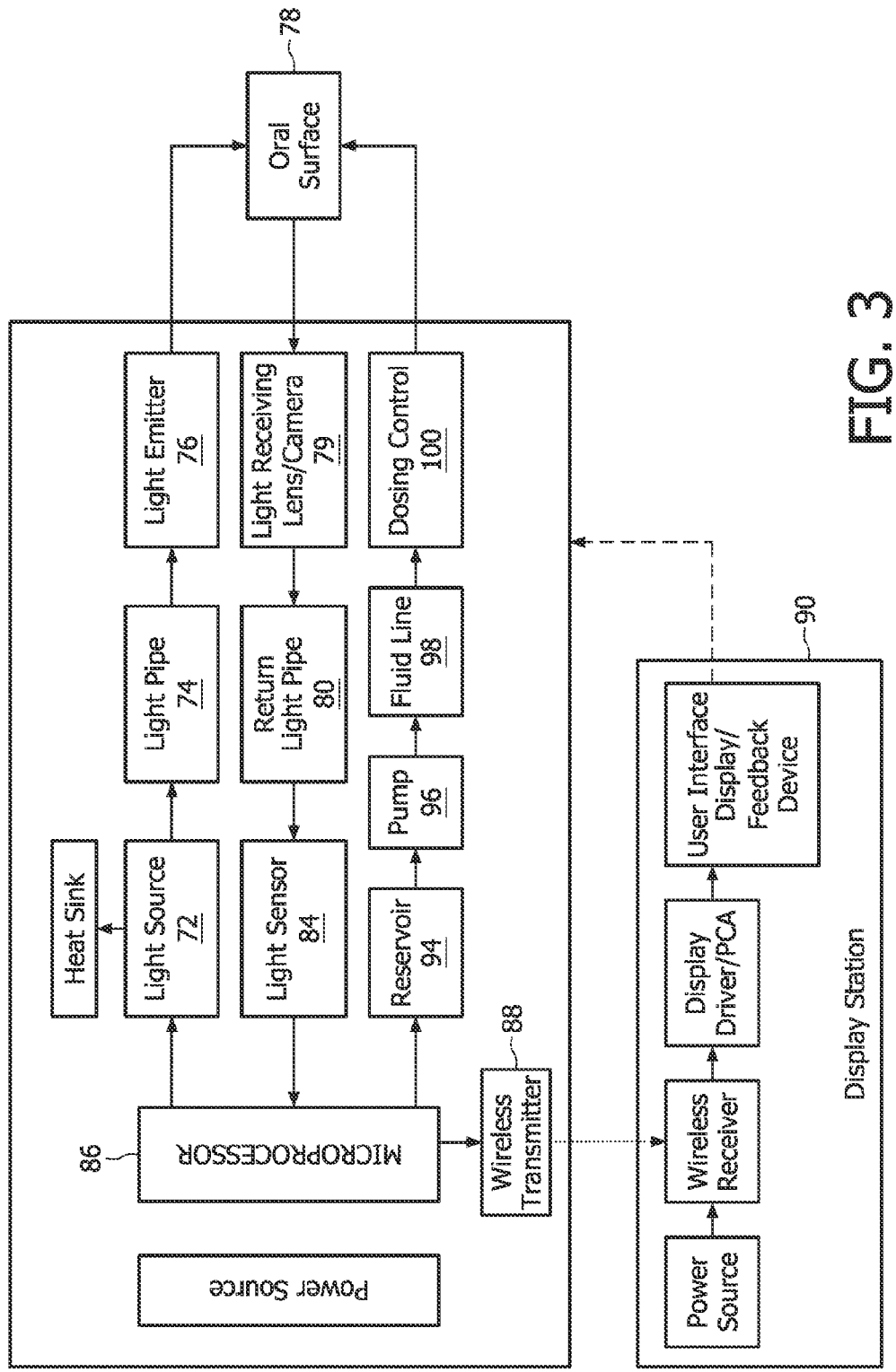
FIG. 3 is a block diagram showing the present system for the detection, healing and coverage of other oral health conditions.

FIG. 3 shows a detection and treatment appliance system for other oral care conditions, including periodontitis, caries and staining of the teeth. It should be understood that other oral care conditions beyond those described herein may also be treatable with the appliance. Also, it should be understood that the arrangements of FIGS. 2 and 3 can be combined into one appliance.

The embodiment of FIG. 3 also includes a light source 72, again in an appropriate wavelength range, for instance the blue spectrum, as well as a portion of the red spectrum, and perhaps others, depending upon the particular oral health condition. The light beam is directed to a transmit light pipe 74 and then to a light emitter 76 in the applicator head portion of the appliance, with the emitted light proceeding to the oral surface 78. Some of the light is absorbed while some is reflected back to the light-receiving lens/camera 79 in the applicator head. The received light is then directed through a return light return pipe 80 and to a light sensor 84, the output of which is applied to a microprocessor 86. The microprocessor 86, using the result from the light sensor, then determines whether any oral health condition is present in the area covered by the light beam, depending on the characteristics, e.g. wavelength/energy, of the reflected light, and then directs the information to the display station 90 by means of wireless transmitter 88. The display station 90 is similar to display station 54 of FIG. 2.

The display station 90 will provide information to the user relative to any oral health conditions in the mouth determined by the microprocessor. The information provided will also include how to treat the condition. The user then has the opportunity to pursue treatment of the identified condition. Light can be used to treat the condition, with light source 72, light pipe 74 and light emitter 76. Light from emitter 76 is directed toward the particular area or areas having the identified oral health condition. The user simply aims the appliance at the affected area. The mapping capability of the appliance can also be used to correctly aim the appliance in the treatment mode. The light source for treatment can be the same or different than the light source used to detect the oral health condition, depending upon the particular oral condition being treated.

A sensitizing solution can also be used, with the solution being a formulation, for instance, which is adapted to enhance the effectiveness of the light, such as by increasing the absorption of light by the plaque or other surface condition. In the fluid treatment mode, fluid is moved from a reservoir 94 by a pump 96, actuated by the microprocessor. The fluid is moved through a fluid line 98 and then through a dosing control unit 100 to the desired area oral surface which has been previously identified. The locating/mapping capabilities of the appliance can be used to assist the user in aiming the appliance.

The embodiment of FIG. 3 can also be used to map the mouth, using light, similar to the embodiment of FIG. 2, determining and identifying to the user which areas of the mouth have been investigated and which have not.

Hence, a system has been described which includes a handheld appliance containing a source of light of selected wavelength capable of identifying different oral health conditions and then providing treatment for the condition through various arrangements, including light, mechanical brushing and fluid treatment. The appliance can be used also to provide a mapping/location capability concerning which regions of the mouth have actually been investigated, providing the user the ability to completely review and treat, if necessary, the condition of the whole dental area. Such a mapping capability makes the appliance appropriate for home use. The appliance can use a single light source for all functions, or multiple light sources, to accomplish different selected functions.

Although a preferred embodiment of the invention has been disclosed here for the purposes of illustration, it should be understood that various changes, modifications and substitutions may be incorporated in the embodiment without departing from the spirit of the invention, which is defined by the claims which follow.

The invention claimed is:

1. An oral care appliance configured for investigation of a user's mouth, comprising:
   a source of light (16) having a wavelength suitable for oral health condition diagnosis and/or treatment;
   an assembly (16, 14, 26) configured for directing the light to the dental region of the mouth, illuminating one or more teeth;
   a light receiver or camera and sensor assembly (16) configured for receiving light reflected from the teeth, the sensor assembly providing output signal information corresponding to the reflected light from said one or more teeth;
   a processor (20) configured for identifying the presence of an oral health condition from the output signal information;
   a memory configured for storing known typical size and location information of teeth in the mouth, wherein the processor is programmed for processing the stored size and location information with the output signal information, to determine those teeth which have been investigated and the location of oral health conditions and/or to identify those areas of the teeth which have not yet been investigated and to provide such information to a display;
   a system (16) configured for treating the identified oral health condition; and
   a display (24) configured for providing to the user information concerning any oral health conditions which have been identified by the processor and information concerning those areas of the teeth which have and/or have not been investigated.

2. The appliance of claim 1, wherein the light from the light source is used to both identify and treat the oral care condition.

3. The appliance of claim 1, wherein the oral health condition is at least one of the following: caries, plaque, periodontitis and staining.

4. The appliance of claim 1, wherein the treating system includes a brushing assembly (66, 68) and a driver (64) for the brushing assembly when the treatment system comprises mechanical brushing of the teeth.

5. The appliance of claim 1, wherein the treating system includes a system for delivery of a fluid effective in treatment of the oral care condition.

6. The appliance of claim 5, wherein the fluid delivery system includes a reservoir (94) for treatment fluid, a pump (96) for pumping the fluid from the reservoir, a fluid line (98) and a dosing control assembly (100) to deliver the fluid to a selected oral surface.

7. The appliance of claim 1, wherein the display is physically separate from the remainder of the appliance.

8. The appliance of claim 7, wherein the display and the processor communicate by wireless transmission.

9. The appliance of claim 1, wherein the light receiver or camera and sensor assembly includes a light-receiving lens or camera, a returning light pipe member and a light sensor.

10. The appliance of claim 1, wherein the display information is in the form of visual information.

11. The appliance of claim 1, wherein the stored information includes all the teeth in the mouth.

12. A method of oral care for a user's mouth with an appliance, comprising the steps of:
   generating light having a wavelength suitable for oral care condition diagnosis and transmitting said light to a selected oral dental surface, illuminating the oral dental surface;
   receiving reflected light from the oral dental surface;
   processing the reflected light by a processor to determine the presence of an oral health condition;
   wherein the processor uses stored information concerning known typical size and location information of teeth in the mouth and output signal information corresponding to the reflected light to accurately identify and display the location of those areas of the teeth which have been investigated and the location of oral health conditions and/or to identify those areas of the teeth which have not yet been investigated;
   displaying to the user information concerning the presence of oral health conditions which have been identified and information concerning those areas of the teeth investigated and/or not yet investigated; and
   treating the oral health condition by a treatment portion of the appliance.

13. The method of claim 12, including the step of treating the oral care condition with light generated within and transmitted from the appliance or by delivery of a fluid capable of treating the oral health condition to the oral surface, or by a brush assembly for mechanically brushing the teeth.

* * * * *